United States Patent [19]

Sullivan

[11] Patent Number: 4,546,778
[45] Date of Patent: Oct. 15, 1985

[54] MOISTURE DETECTOR FOR RESPIRATORY MONITORING SYSTEMS

[75] Inventor: Richard E. Sullivan, Berkeley, Calif.

[73] Assignee: Critikon, Inc., Tampa, Fla.

[21] Appl. No.: 498,424

[22] Filed: May 26, 1983

[51] Int. Cl.$^4$ ............................................. A61B 5/08
[52] U.S. Cl. .................................. 128/718; 128/719;
    73/863.21; 340/620; 422/84
[58] Field of Search ........................ 128/716, 718–719;
    55/215; 73/863.21; 340/620; 422/83–84

[56] References Cited

U.S. PATENT DOCUMENTS

| | | | |
|---|---|---|---|
| 2,636,927 | 4/1953 | Durham | 324/65 R |
| 3,935,742 | 2/1976 | Rybak | 73/336.5 |
| 4,087,743 | 5/1978 | Bressan | 324/427 |
| 4,197,858 | 4/1980 | Osborn | 128/718 |
| 4,246,676 | 1/1981 | Hallsworth et al. | 55/215 X |
| 4,264,901 | 4/1981 | Peterson et al. | 340/604 |
| 4,270,564 | 6/1981 | Blackburn et al. | 137/240 |
| 4,459,266 | 7/1984 | Lamoreaux | 128/719 X |
| 4,465,485 | 8/1984 | Kashmer et al. | 55/215 X |

Primary Examiner—Lee S. Cohen
Assistant Examiner—Angela D. Sykes
Attorney, Agent, or Firm—Audley A. Ciamporcero, Jr.

[57] ABSTRACT

A system for monitoring patient respiration include a disposable, convenient moisture detection device. The device is minimally intrusive to the laminar flow of gases and has minimal liquid collection volumes. It is characterized by high sensitivity at rapid response rates.

4 Claims, 5 Drawing Figures

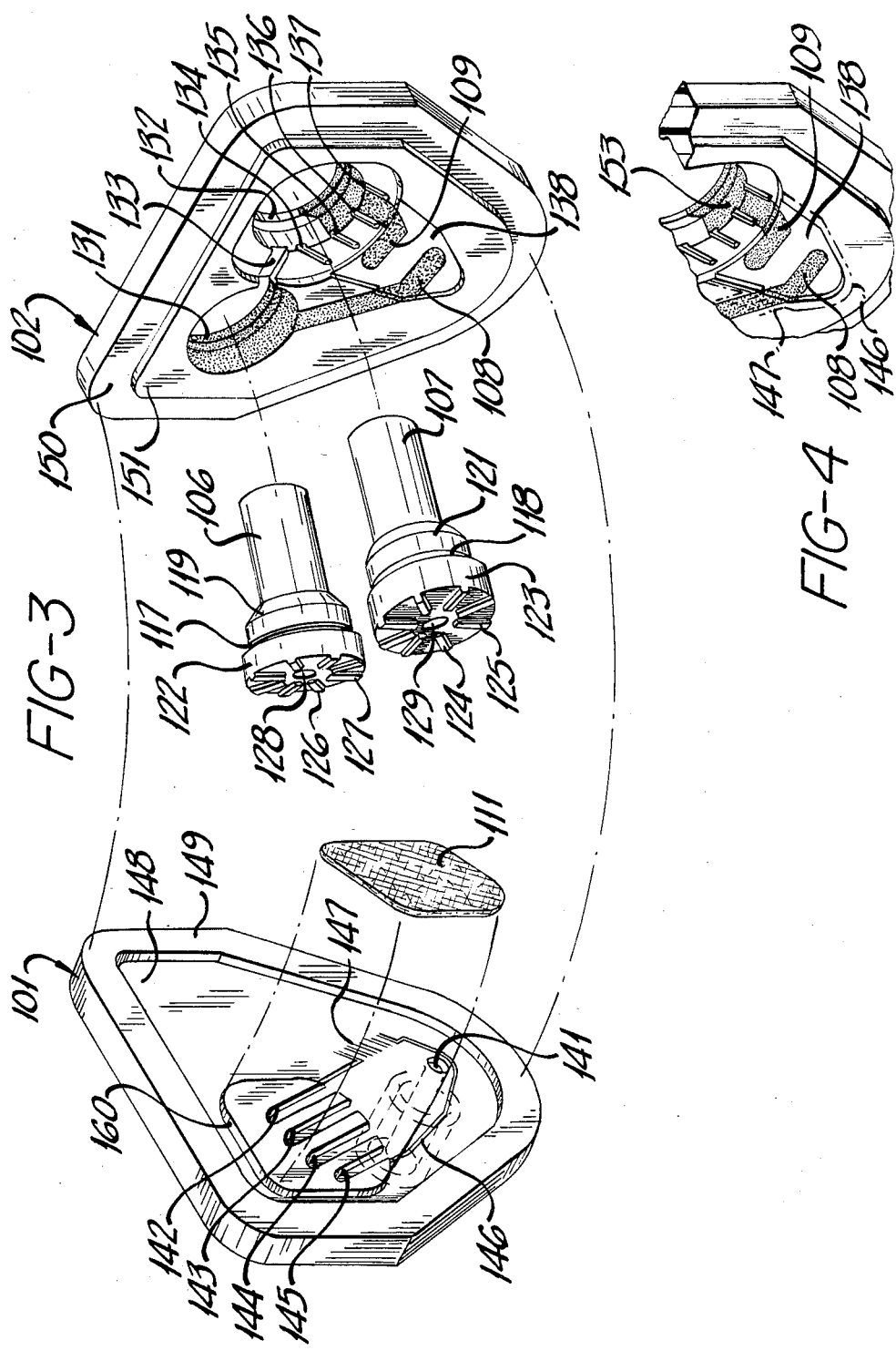

MOISTURE DETECTOR FOR RESPIRATORY MONITORING SYSTEMS

FIELD OF THE INVENTION

This invention relates to systems for monitoring patient respiration, and more particularly to detectors which sense the presence of excessive fluid in the monitoring path.

BACKGROUND OF THE INVENTION

Respiratory monitoring is becoming an increasingly important tool in the monitoring, analysis, and treatment of the critical care patient. For example, anesthesiologists in the operating theatre, and attending physicians and nurses in intensive care and critical care units, depend more and more on respiratory monitoring as an essential indicator of the condition of the patient. Not surprisingly, increased frequency of use of respiratory monitoring techniques, tends to expand the method to more diverse populations of patients, and thus to place increasingly severe demands on the systems themselves, and upon those subsystems which avoid malfunction or system error. For example, there exists a wide disparity in respiratory quotient among patients of varying age (i.e., from neonate to octogenarian), physique, and relative robust health status. The respiratory monitoring systems themselves must be capable of responding to the widely varying parameters which are so involved, and so also must the subsystems avoid mistaking a malfunction or blockage artifact as a patient condition.

Conventional patient gas sampling systems include moisture detection devices designed to detect unwanted liquid transported from the patient. That is, conventional systems have the capacity to sense and measure vapor partial pressure of expired gases, and such readings would be severely compromised if free liquid, mucous, or the like materials were exposed to or lodged in the sensor. Thus, these systems have a need for, and generally include various sorts of devices which accumulate liquid at some point intermediate the patient and the analyzer, and which have the capacity for line purging once a predetermined amount of liquid has become entrapped. Generally, these devices need to be compact, low volume, disposable, and minimally intrusive to the flow of gases from the patient to the analyzer. Ideally, the structure and volume of the devices support laminar flow conditions, and avoid fluid mixing and consequent dilution of the gas "signal" to be measured and analyzed. Prior art examples of such devices include those set forth in U.S. Pat. Nos. 4,197,858 to Osborn, and 4,270,564 to Blackburn et al.

It is a primary object of the present invention to provide disposable, convenient moisture detection devices for respiratory monitoring systems, which are minimally intrusive to the laminar flow of gases, which have minimal liquid collection volumes, and are characterized by high sensitivity at very rapid response rates.

SUMMARY OF THE INVENTION

In accordance with the principles of the present invention, a two-part molded housing fits together essentially to define a laminar flow path which is of insignificant volume with respect to the passageway, and which includes integral conductive nipple fittings and conductive divider bridge arms such that moisture buildup is quickly and accurately sensed. In particular, the housing defines a passageway which is normal to the respiratory inlet, outlet, and purge ports, and yet which minimally alters gas flow. In preferred form, the entire unit is disposable, and yet highly effective.

DESCRIPTION OF THE DRAWINGS

FIG. 3 shows a dual perspective, further exploded version; FIG. 4 shows a partial cutaway of the apparatus of FIG. 3.

BEST MODE OF CARRYING OUT THE INVENTION

Figure 5:
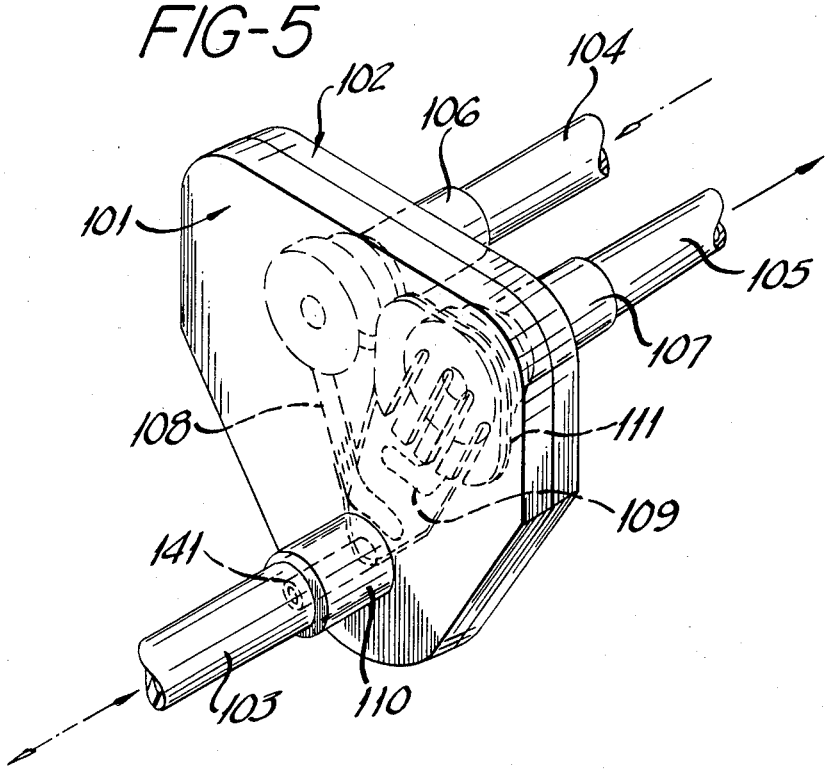
FIG. 5 shows in partial transparency a preferred embodiment of the principles of the present invention.
Figure 1:
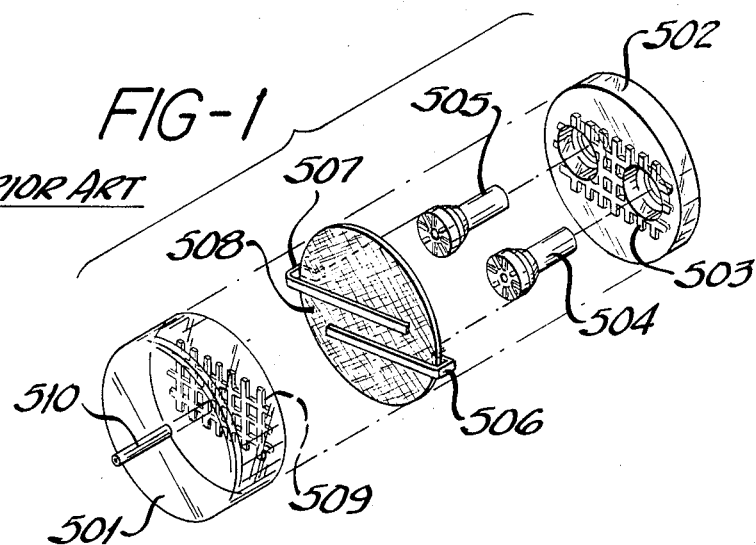
FIG. 1 shows a prior art version.

As will be noted from the foregoing, the issued U.S. patents to Osborn and to Blackburn et al. typify prior art approaches to the design of moisture traps and purging systems. The Osborn patent, which is owned by the assignee hereof, features a design upon which the principles of the present invention are designed to improve. In FIG. 1, there is shown another sort of prior device, which in many respects represents an earlier stage in the evolution of the principles of the present invention. In the FIG. 1 embodiment, a hydrophilic filter element 508 is embraced by a pair of rigid conductive leads 506 and 507, which wrap around the filter element 508. A port 510 is coupled to the patient airway, and delivers expired respiration from the patient through a first half 501, which half is formed of a potting material and which defines a grid of channels 509. A second half 502 carries a corresponding grid of channels 503, and defines therein a pair of openings for receipt of a corresponding pair of conductive nipples 504 and 505. The two potted halves 501 and 502 are sandwiched over the filter medium 508 such that the conductive nipples 504 and 505 make respective contact with the lead elements 506 and 507. The entire assembly is bonded together, and in the normal course expired gases enter by way of port 510, are distributed through the grid 509, and then pass through the filter element 508, to be delivered via exhaust nipple 504 to an analyzer system. A separate nipple 505 is coupled to a purge system (not shown). In operation, the conductive nipples 504 and 505 are coupled to a bridging circuit (not shown) and when sufficient fluid accumulates in the inlet channel grid 509 to alter the bridging potential in predetermined fashion, the analyzer temporarily closes the exhaust channel, and through application of pressurized gases from the purge system via nipple 505, causes a dispersion and removal of the accumulated fluids.

The prior art system of FIG. 1 embodies the germ of certain good ideas, but in fact falls short of the mark as an effective fluid sensor and trap pursuant to the objects of the present invention. In particular, air leakage at the leads 506 and 507, a difficult to manufacture yet relatively intrusive system of channels, and a difficult and expensive manufacturing process characterize that design. More importantly, the overly large volume of the channels combined with uneven flow distributions therein, tend to force a tardiness of response of the overall system. The embodiment of FIG. 1 accordingly provides a separate basis upon which the principles of the present invention are designed to improve.

FIGS. 2 through 5, inclusive, show a variety of views of preferred embodiments of the principles of the present invention, some in partial transparency, others in exploded componentry, and one (FIG. 2) illustrating appropriate interconnection with conventional monitoring and analysis apparatus. Throughout FIGS. 2 through 5 inclusive, the same components and portions are allocated similar numbers, thereby facilitating an understanding not only of the overall configuration of the unit, but also suggesting appropriate manufacturing techniques to be employed.

Referring in general, then, to FIGS. 2 through 5 inclusive, it is seen that the housing of the moisture detector/trap is formed of a pair of opposing, matable halves 101 and 102. Half 101 is coupled, via sleeve 110 and inlet port 141, to the patient airway, in particular in a fashion to permit receipt and analysis of expired patient gases. The other half 102 is coupled, via lines 104 and 105, to the analyzer itself. In particular, a pair of openings in the second half 102 carries a corresponding pair of conductive nipples 106 and 107, each of which defines a respective port 128 and 129 therethrough. The nipple 106 is coupled to a purge or flush line 104 from the analyzer, and the nipple 107 is coupled to exhaust and analysis line 105. Thus, in the normal course, under control of microprocessor 112, the purge pump 115 in the analyzer is disabled, valve 114 in the analyzer is closed, and no gases are provided to the trap through purge line 104. Gases from the trap, in particular from nipple 107, are coupled via line 105 through a normally open valve 113 to the analyzing sensors 110, all driven by sampling pump 116. On the other hand, at such time as a purge is called for, valve 113 is closed and pump 116 is disabled, valve 114 is open and pump 115 is activated, and a flush of purge gas is delivered to nipple 106.

Figure 2:
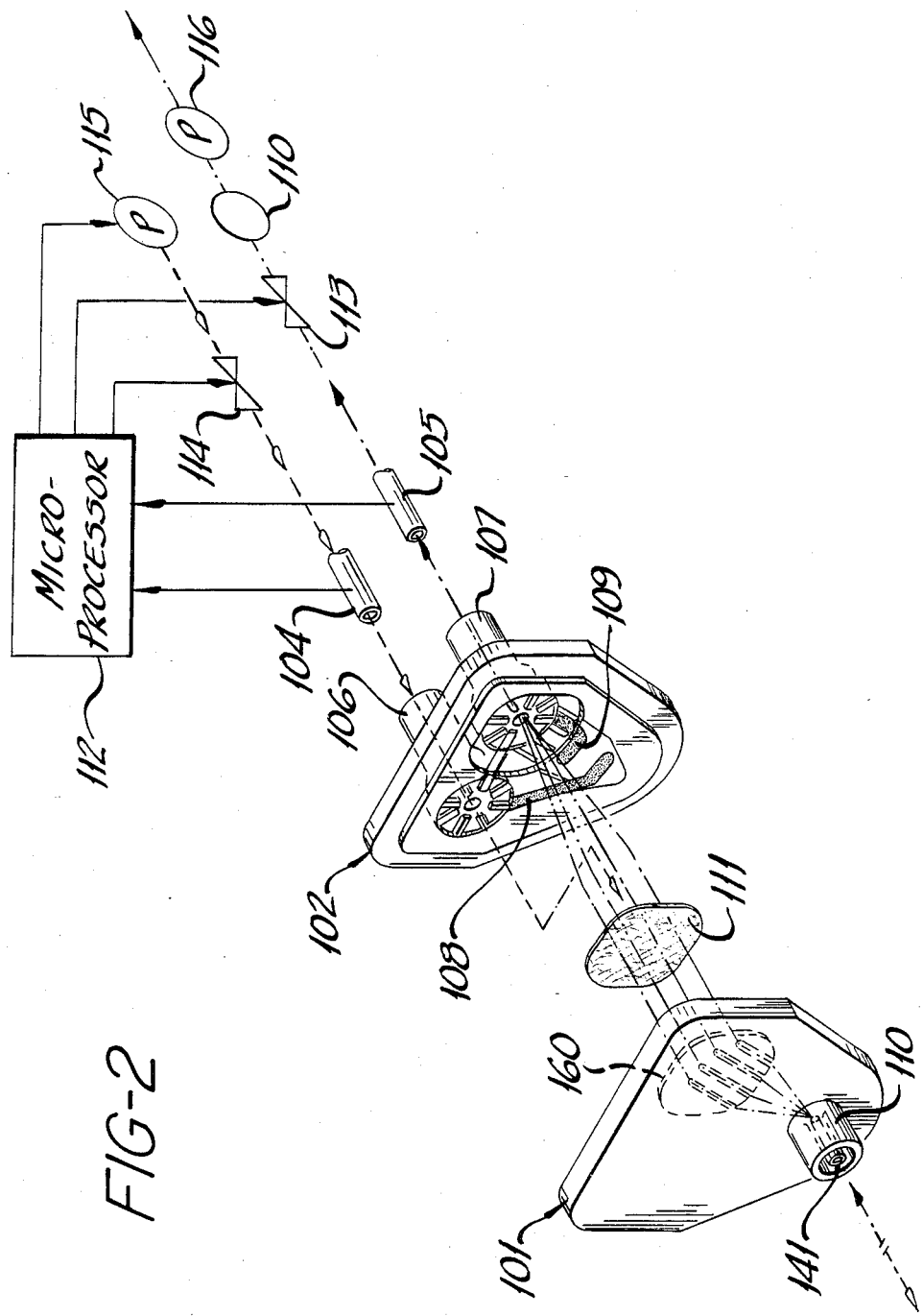
FIG. 2 shows an exploded view of the embodiment of FIG. 5, further including symbolic interconnections with an analyzer circuit.

It is to be noted that the operation of the microprocessor 112, valves 113 and 114, pumps 115 and 116, and sensors 110, are all standard operations in the prior art, and constitute only an environmental aspect of the principles of the present invention. As shown in FIG. 2, the purge channel 104 and the exhaust/sensing channel 105 are both electrically coupled to the microprocessor. In conventional usage, this electrical connection is provided to one arm of a bridge circuit, which monitors fluid buildup in a moisture trap, and which upon predetermined potential imbalance conditions, indicates the need to interrupt sampling operation and to run a purge cycle.

It is noted that the moisture trap halves 101 and 102 are themselves matable for hermetic seal upon assembly. To this end, the first half 101 defines a depression 148 and a surrounding ridge 149, which mates with a channel 150 and raised land 151 in the second half 102. In preferred embodiments, both halves 101 and 102 are configured of thermoplastic materials which are easily and sealably bonded together, for example by ultrasonic welding techniques. Of course, those skilled in the art will be free to apply numerous alternative weldment and bonding techniques. Likewise, the choice of materials themselves will be subject to wide variation pursuant to the discretion of designers of ordinary skill.

The second half 102 is seen to define a pair of annular ridges 131 and 132 in each of the openings, for matable fit with respective channels 117 and 118 in the conductive elastomeric nipples 106 and 107. Thus, each of the nipples 106 and 107 may be forcefit into the second half 102, with the ridges 131 and 132 nested in the associated channels 117 and 118. In preferred embodiments, each of the nipples 106 and 107 is composed of a deformable conductive rubber composition, and hence when the niples 106 and 107 are positioned in the second housing half 102, each will be engaged in a sealed condition through the raised portions defining the channels 117 and 118, those being numbered 119 and 122 in the case of flush nipple 106, and being numbered 121 and 123 in the case of exhaust/sampling nipple 107.

As will be further noted from the drawings, a pair of conductive bridge arm traces 108 and 109 are applied, for example through printing processes, for electrical connection to the conductive nipples 106 and 107. It will be appreciated from consideration of FIG. 2 that this in turn establishes a connection to the microprocessor 112 via the lines 104 and 105. In particular, bridge arm trace 108 extends up to and through the housing opening and through physical contact is electrically coupled with the purge nipple 106. Bridge arm 109 extends up to and in contact with, and is hence electrically coupled to the exhaust/sampling nipple 107.

Both bridge arm traces 108 and 109 extend down into a channel through which sampling gases pass from the inlet port 141 to the exhaust/sampling port 129. This channel is seen to be formed by a raised land 146 within well 148 of the first housing half 101, and a corresponding depression 138 on the raised land 150 of the second housing half 102. When the two halves 101 and 102 are suitably bonded together, the raised land 146 sealably encloses the depression 138 and forms a channel for passage of gases from opening 141 to opening 129. It will be noted that the first half 101 defines a generally square projection 160, which is designed to abut a filter element 111. A corresponding well is found in the second half 102, which encloses the filter element 111. The projection 160 defines channels 142 through 145, inclusive, each of which spatially overlies, but is separated by filter element 111 from respective opposing channels 134 through 137, inclusive, on the second half 102.

It will be noted that both nipples 106 and 107 define a series of radial lands such as 124 and 125 on nipple 107, and 126 and 127 on nipple 106. As the housing is bonded together, the filter element 111 nests between the projection 160 and lands 124, 125, etc. on the exhaust/sampling nipple 107. Thus, in the normal course, gases enter via port 141, pass up along through the channel formed by depression 138 and land 146, into the channels 142 through 145, inclusive, through the filter 111, and thence either through channels 134-137, or directly via the spaces between radial lands 124 and 125, to and through the exhaust/sampling port 129.

The actual moisture sensor and trap is therefore the space in depression 138 below and between the bridging arm traces 108 and 109. As fluid tends to accumulate in that space, to the extent of creating a physical bridging of the arm traces 108 and 109 and establishing a potential imbalance as sensed in the bridge circuit at the microprocessor 112, a flush condition is called for. Thereupon, as stated hereinbefore, the pump and valve 113 and 116 in the exhaust/sampling line is cut off, and valve 114 is opened and pump 115 is actuated to commence a purging or flushing operation. Such purging gases enter the trap through purging port 128, and are coupled via purge channel 133 to the distal side (i.e., the side adjacent the nipple 107) of the filter element 111. Since valve 113 then is closed, the purging gases pass back through the filter element, down through the trap channel formed by depression 138, and back out through the inlet port 141. This purging continues until the microprocessor 112, by monitoring bridging arms 108 and 109, determines that the accumulated liquid is no longer bridging the electrical traces 108 and 109. After a short predetermined additional period of time, the process is reversed, pump 115 is disabled and pump 116 is enabled, valve 114 is closed and valve 113 is opened, and sampling and analysis continues.

It will be further noted from consideration of FIG. 3 that the land 146 defines "feathering" portions 147. It has been found empirically that the feathering portions 147 are beneficial to avoid weldthrough of the conductive trace 108 when ultrasonic bonding is being employed to join halves 101 and 102. The feathering 147 provides in essence an energy director over the conductive bridging arm trace 108, so that any extra welding energy is taken up by the extra plastic of the feathering 147, rather than being directed to and through, and breaking up the electrical trace 108.

The embodiment shown in the figures may therefore be simply manufactured, with the respective halves 101 and 102 being formed, as by injection molding, and the conductive coatings being applied for formation of bridge elements 108 and 109. The nipples 106 and 107 are then sealably forcefit into the second half 102, the filter element 111 is inserted into the accommodating space therefor, and the two halves are ultrasonically welded together.

Considering the embodiment of FIGS. 2-5 inclusive, in terms of form and function, it will be seen that embodiments of the principles of the present invention are well and adequately addressed to general goals and objects for apparatus of the type. In particular, the device involves a very low volume (e.g., 0.1 millileter) trap which is configured for well-calibrated operation at high response rates. In particular, in normal use the housing has a generally vertical orientation, and the channel therein, through which gases flow, is likewise generally vertically oriented. The lowermost portion of the channel forms a well or reservoir for fluids, and as those fluids build up past the lowermost conductive trace toward the uppermost trace, the need for purge approaches. When fluids actually create a conductive bridge between the traces, a balanced bridge circuit in the microprocessor causes the purge cycle, previously described, to be performed. It will be noted that the slots 142-145, inclusive, in the first half 101, and the corresponding slots 134-137, inclusive, in the second half 102, promote laminar flow by directing gases passing upwardly thrugh the channel to and through the filter medium 111, and out the exhaust port 129. Likewise, utilization of printed traces 108 and 109 on the sidewall of the channel obviate leakage and accumulation of the fluids and the like on the bridge sensing electrodes. An integral flush port 133 provides minimal intrusion into the normal sampling and analysis process, and hence allows the overall volume of the channel to be kept at a minimum.

It will be appreciated that the foregoing defines preferred and illustrative embodiments of the principles of the present invention, but that numerous alternative embodiments will occur to those of ordinary skill in the art without departure from the spirit or scope of the present invention. For example, the embodiment set forth is compact (approximately one inch by inch one by one-quarter inch overall), but it may be that application of the same principles will allow for even further reduction in size of the embodiments.

What is claimed is:

1. In a respiratory gas analysis system, a trap for avoiding unwanted fluid accumulation comprising:
   (a) a housing having a generally vertical orientation, having an entry port on one side at a relatively lower extremity, and having an exhaust port on an opposite side at a relatively upper extremity:
   (b) said housing defining therein a generally vertical channel having walls extending from below said entry port at least up to said exhaust port, said channel having relatively minimal cross sectional dimension between said opposite sides:
   (c) a pair of conductive traces each applied to a wall of said channel, one trace being located at a lower part of said channel, and the other trace having a predetermined location below said one trace on said entry port of said channel:
   (d) said housing further defining a flush port for coupling purge gases to said channel at a point above said other trace.

2. Apparatus as described in claim 1 and further including a filte medium disposed over said exhaust port.

3. Apparatus as described in claim 2 wherein said flush port enters said channel intermediate said filter medium and said exhaust port.

4. Apparatus as described in claim 3 wherein said filter medium is disposed generally vertically, and wherein said housing defines plural flow directing channels on both sides of said filter medium to promote laminar flow from said channel, to and through said filter medium, and to and through said exhaust port.

* * * * *